(12) United States Patent
Möckel et al.

(10) Patent No.: US 6,939,694 B2
(45) Date of Patent: Sep. 6, 2005

(54) NUCLEOTIDE SEQUENCES WHICH CODE FOR THE CITB GENE

(76) Inventors: Bettina Möckel, Benrodestrasse 35, D-40597 Düsseldorf (DE); Thomas Hermann, Zirkonstrasse 8, D-33739 Bielefeld (DE); Mike Farwick, Gustav-Adolf-Strasse 11, D-33615, Bielefeld (DE); Walter Pfefferle, Jahnstrasse 33, D-33790 Halle (Westf.) (DE); Achim Marx, Altenbrede 4B, D-33613 Bielefeld (DE)

(*) Notice: Subject to any disclaimer, the term of this patent is extended or adjusted under 35 U.S.C. 154(b) by 608 days.

(21) Appl. No.: 09/942,937

(22) Filed: Aug. 31, 2001

(65) Prior Publication Data

US 2002/0086372 A1 Jul. 4, 2002

(30) Foreign Application Priority Data

Aug. 31, 2000 (DE) .......................... 100 42 741
Feb. 23, 2001 (DE) .......................... 101 08 841

(51) Int. Cl.[7] .......................... C12N 9/88; C12N 15/00; C12N 1/20; C12N 5/00; B07H 21/04
(52) U.S. Cl. ............. 435/115; 435/252.32; 435/252.33; 435/320.1; 435/69.1; 435/325; 435/232; 435/4; 536/23.1; 536/23.2
(58) Field of Search .................. 435/232, 4, 69.1, 435/325, 252.3, 252.32, 320.1, 252.33; 536/23.2, 23.1

(56) References Cited

PUBLICATIONS

Bork, Genome Research, 10:348–400, 2000.*
Broun et al., Science 282:1315–1317, 1998.*
Van de Loo et al., Proc. Natl. Acad. Sci. 92:6743–6747, 1995.*
Todo et al., GenEMBL accession No. AF265258, May 30, 2000.*
Ikeda et al., Appl. Environ. Microbiol., 65:2494–2502, 1999.*
Sambrook et al., Molecular Cloning, Second Edition, CSHL Press, 1989.*
Seffernick et al., J. Bacteriol. 183(8):2405–2410, 2001.*
Michael Bott, et al., "Regulation of anaerobic citrate metabolism in Klebsiella pneumoniae", Molecular Microbiology (1995) 18(3), pp. 533–546.
Paul Golby, et al., "Identification and Characterization of a Two–Component sensor–Kinase and Response–Regulator system (DcnS–DcnR) Controlling gene Expression in Response to $C_4$–Dicarboxylates in *Escherichia coli*", Journal of Bacteriology, pp. 1238–1248 (Feb. 1999).

* cited by examiner

*Primary Examiner*—Rebecca E. Prouty
*Assistant Examiner*—Delia Ramirez
(74) *Attorney, Agent, or Firm*—Smith, Gambrill & Russell, LLP

(57) ABSTRACT

The invention relates to an isolated polynucleotide having a polynucleotide sequence which codes for the citB gene, and a host-vector system having a coryneform host bacterium in which the citB gene is present in attenuated form and a vector which carries at least the citB gene according to SEQ ID No 1, and the use of polynucleotides which comprise the sequences according to the invention as hybridization probes.

11 Claims, 1 Drawing Sheet

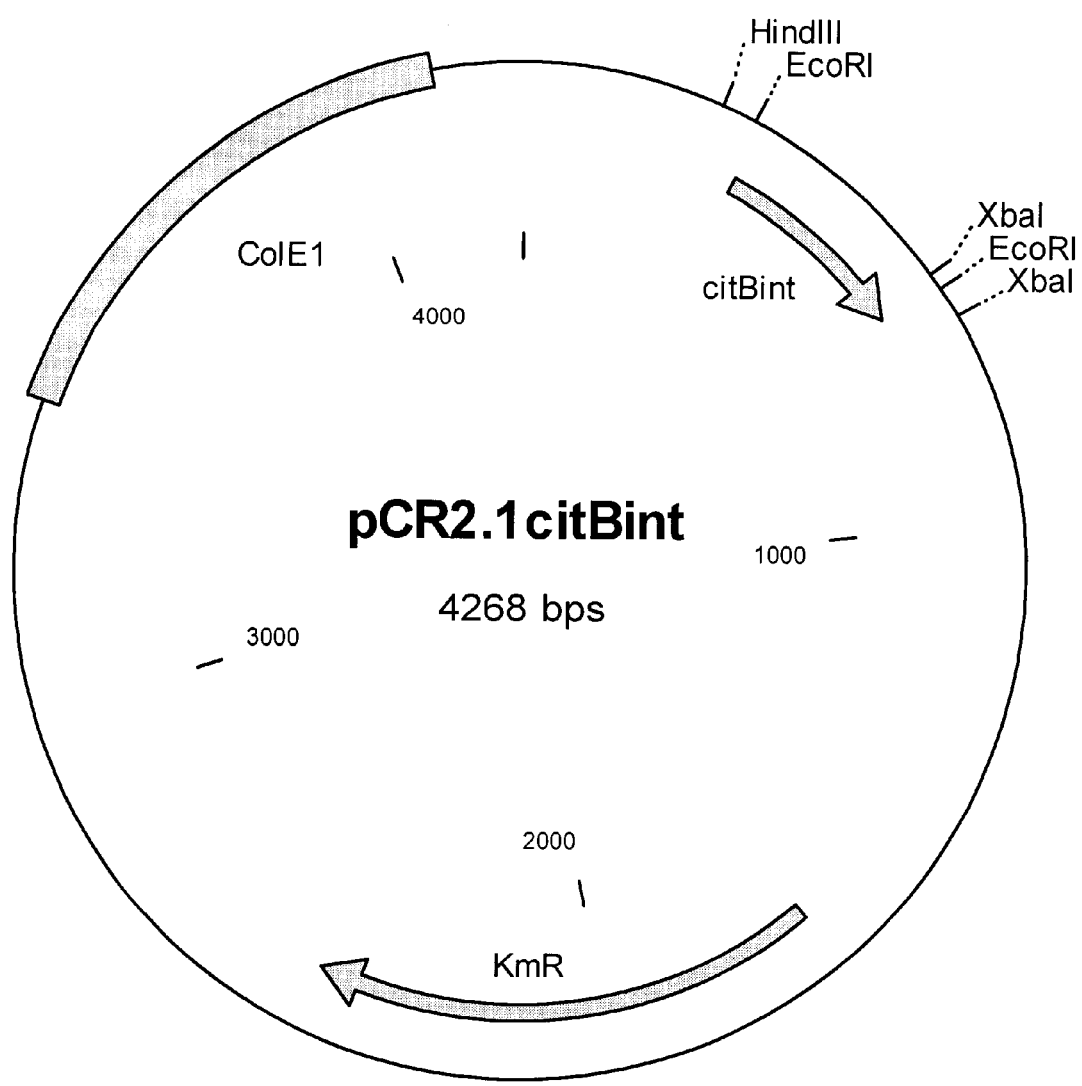

SEQUENCE LISTING

<160> NUMBER OF SEQ ID NOS: 5

<210> SEQ ID NO 1
<211> LENGTH: 1056
<212> TYPE: DNA
<213> ORGANISM: Corynebacterium glutamicum
<220> FEATURE:
<221> NAME/KEY: CDS
<222> LOCATION: (201)..(854)
<223> OTHER INFORMATION:

<400> SEQUENCE: 1

```
atcccagagg gcgtggatgt atttgccaca gccacccaga taggagactc tgaagataat      60
gaacgcaccc acgggcatgg cattggtcta aaactgtgcc gggctttggc tagatcacat     120
ggtggcgatg tctgggtgat tgatagagga accgaagatg gcgctgtatt tggagtgaaa     180
ctaccgggag taatggagta atg gat caa aca ctt aaa gtt tta gta att gat    233
                        Met Asp Gln Thr Leu Lys Val Leu Val Ile Asp
                         1               5                  10 gat gat ttc cgc gtc gcc ggc att cac gcc tcc atc gtt gat gcg tcc      281
Asp Asp Phe Arg Val Ala Gly Ile His Ala Ser Ile Val Asp Ala Ser
         15                  20                  25 cct gga ttt tcg gtg gtc ggt acc gcg cgt acc ctc gca gag gca aaa      329
Pro Gly Phe Ser Val Val Gly Thr Ala Arg Thr Leu Ala Glu Ala Lys
     30                  35                  40 acc ctg atc gcc aca ttt tcc ccg gat ctc cta ctt gtt gat gtc tac      377
Thr Leu Ile Ala Thr Phe Ser Pro Asp Leu Leu Leu Val Asp Val Tyr
 45                  50                  55 ctc ccc gac ggc gat ggc att gac ctc gtg ggc acc tcc aat att gat      425
Leu Pro Asp Gly Asp Gly Ile Asp Leu Val Gly Thr Ser Asn Ile Asp
 60                  65                  70                  75 gcg ttt gtg ctc agc gca gcc gat gac atc aaa aca gtt cga cgc gcc      473
Ala Phe Val Leu Ser Ala Ala Asp Asp Ile Lys Thr Val Arg Arg Ala
                 80                  85                  90 atg cgt gcc ggg gca ctc gga tat ctg ctc aaa cca ttt ccc caa aaa      521
Met Arg Ala Gly Ala Leu Gly Tyr Leu Leu Lys Pro Phe Pro Gln Lys
             95                 100                 105 cgt ctc gtg gaa cgc ctt gac cgt tac gtc cgc tac cgc cat gtc tta      569
Arg Leu Val Glu Arg Leu Asp Arg Tyr Val Arg Tyr Arg His Val Leu
        110                 115                 120 tcc ggc acc caa gga ctt tcc caa gac aaa att gac cag gca acc gca      617
Ser Gly Thr Gln Gly Leu Ser Gln Asp Lys Ile Asp Gln Ala Thr Ala
    125                 130                 135 atc ctc aac ggc acc caa gcg ccg gtc acc gtc tct aga tcc gcc aca      665
Ile Leu Asn Gly Thr Gln Ala Pro Val Thr Val Ser Arg Ser Ala Thr
140                 145                 150                 155 gag caa tta ctt ctc gac gcc ctg gaa ggc caa gaa ctc tcc gca aca      713
Glu Gln Leu Leu Leu Asp Ala Leu Glu Gly Gln Glu Leu Ser Ala Thr
                160                 165                 170 gaa gct tcc gaa gct gcc gga gtt tca cgt gcc aca gca cag cgc agg      761
Glu Ala Ser Glu Ala Ala Gly Val Ser Arg Ala Thr Ala Gln Arg Arg
            175                 180                 185 ctg gca gcg atg gct agc caa ggt gtg atc cag gtt cgc ctt cgg tac      809
Leu Ala Ala Met Ala Ser Gln Gly Val Ile Gln Val Arg Leu Arg Tyr
        190                 195                 200 gga cag tcc ggg cga cca gaa cat cta tat tca aag cca ctg ctc          854
Gly Gln Ser Gly Arg Pro Glu His Leu Tyr Ser Lys Pro Leu Leu
    205                 210                 215 tagtaacctt tgtggatgtc cacctcggtc agcatctttt ctccagcgag aaaccgtcgg    914
```

```
tagttttctg ccaccactgg ggcaagcatg cgatccatcg aggtcaacgt gttggctacg      974
tgcggggtaa tgatcacatt gctgcgcccc cacagtggat gatcgtccgg caatggttca     1034
ggatcggtga catctaagcc tg                                              1056
```

<210> SEQ ID NO 2
<211> LENGTH: 218
<212> TYPE: PRT
<213> ORGANISM: Corynebacterium glutamicum

<400> SEQUENCE: 2

```
Met Asp Gln Thr Leu Lys Val Leu Val Ile Asp Asp Phe Arg Val
 1               5                  10                  15

Ala Gly Ile His Ala Ser Ile Val Asp Ala Ser Pro Gly Phe Ser Val
            20                  25                  30

Val Gly Thr Ala Arg Thr Leu Ala Glu Ala Lys Thr Leu Ile Ala Thr
        35                  40                  45

Phe Ser Pro Asp Leu Leu Val Asp Val Tyr Leu Pro Asp Gly Asp
    50                  55                  60

Gly Ile Asp Leu Val Gly Thr Ser Asn Ile Asp Ala Phe Val Leu Ser
65                  70                  75                  80

Ala Ala Asp Asp Ile Lys Thr Val Arg Arg Ala Met Arg Ala Gly Ala
                85                  90                  95

Leu Gly Tyr Leu Leu Lys Pro Phe Pro Gln Lys Arg Leu Val Glu Arg
            100                 105                 110

Leu Asp Arg Tyr Val Arg Tyr Arg His Val Leu Ser Gly Thr Gln Gly
        115                 120                 125

Leu Ser Gln Asp Lys Ile Asp Gln Ala Thr Ala Ile Leu Asn Gly Thr
    130                 135                 140

Gln Ala Pro Val Thr Val Ser Arg Ser Ala Thr Glu Gln Leu Leu Leu
145                 150                 155                 160

Asp Ala Leu Glu Gly Gln Glu Leu Ser Ala Thr Glu Ala Ser Glu Ala
                165                 170                 175

Ala Gly Val Ser Arg Ala Thr Ala Gln Arg Arg Leu Ala Ala Met Ala
            180                 185                 190

Ser Gln Gly Val Ile Gln Val Arg Leu Arg Tyr Gly Gln Ser Gly Arg
        195                 200                 205

Pro Glu His Leu Tyr Ser Lys Pro Leu Leu
    210                 215
```

<210> SEQ ID NO 3
<211> LENGTH: 318
<212> TYPE: DNA
<213> ORGANISM: Corynebacterium glutamicum

<400> SEQUENCE: 3

```
cccggatctc ctacttgttg atgtctacct ccccgacggc gatggcattg acctcgtggg       60
cacctccaat attgatgcgt ttgtgctcag cgcagccgat gacatcaaaa cagttcgacg      120
cgccatgcgt gccggggcac tcggatatct gctcaaacca tttccccaaa aacgtctcgt      180
ggaacgcctt gaccgttacg tccgctaccg ccatgtctta tccggcaccc aaggactttc      240
ccaagacaaa attgaccagg caaccgcaat cctcaacggc acccaagcgc cggtcaccgt      300
ctctagatcc gccacaga                                                   318
```

<210> SEQ ID NO 4

```
-continued

<211> LENGTH: 20
<212> TYPE: DNA
<213> ORGANISM: Corynebacterium glutamicum

<400> SEQUENCE: 4
cccggatctc ctacttgttg                                           20

<210> SEQ ID NO 5
<211> LENGTH: 20
<212> TYPE: DNA
<213> ORGANISM: Corynebacterium glutamicum

<400> SEQUENCE: 5
tctgtggcgg atctagagac                                           20
```

NUCLEOTIDE SEQUENCES WHICH CODE FOR THE CITB GENE

BACKGROUND OF THE INVENTION

The invention provides nucleotide sequences from coryneform bacteria which code for the citB gene and a process for the fermentative preparation of amino acids, in particular L-lysine, by attenuation of the citrate utilization gene B (citB gene). The citB gene codes for the CitB protein, which is a transcription regulator of a two-component system. All references cited herein are expressly incorporated by reference. Incorporation by reference is also designated by the term "I.B.R." following any citation.

L-Amino acids, in particular L-lysine, are used in human medicine and in the pharmaceuticals industry, in the foodstuffs industry and very particularly in animal nutrition.

It is known that amino acids are prepared by fermentation from strains of coryneform bacteria, in particular *Corynebacterium glutamicum*. Because of their great importance, work is constantly being undertaken to improve the preparation processes.

Improvements to the process can relate to fermentation measures, such as, for example, stirring and supply of oxygen, or the composition of the nutrient media, such as, for example, the sugar concentration during the fermentation, or the working up to the product form by, for example, ion exchange chromatography, or the intrinsic output properties of the microorganism itself.

Methods of mutagenesis, selection and mutant selection are used to improve the output properties of these microorganisms. Strains which are resistant to antimetabolites or are auxotrophic for metabolites of regulatory importance and which produce amino acids are obtained in this manner.

Methods of the recombinant DNA technique have also been employed for some years for improving the strain of *Corynebacterium* strains which produce L-amino acids.

The invention provides new measures for improved fermentative preparation of amino acids, in particular L-lysine.

BRIEF SUMMARY OF THE INVENTION

If L-lysine or lysine are mentioned in the following, this also means the salts, such as e.g. lysine monohydrochloride or lysine sulfate.

The invention provides an isolated polynucleotide from coryneform bacteria, comprising a polynucleotide sequence which codes for the citB gene chosen from the group consisting of
a) polynucleotide which is identical to the extent of at least 70% to a polynucleotide which codes for a polypeptide which comprises the amino acid sequence of SEQ ID No. 2,
b) polynucleotide which codes for a polypeptide which comprises an amino acid sequence which is identical to the extent of at least 70% to the amino acid sequence of SEQ ID No. 2,
c) polynucleotide which is complementary to the polynucleotides of a) or b), and
d) polynucleotide comprising at least 15 successive nucleotides of the polynucleotide sequence of a), b) or c),
the polypeptide preferably having the activity of the citB protein.

The invention also provides the above mentioned polynucleotide, this preferably being a DNA which is capable of replication, comprising:

(i) the nucleotide sequence shown in SEQ ID No. 1 or
(ii) at least one sequence which corresponds to sequence (i) within the range of the degeneration of the genetic code, or
(iii) at least one sequence which hybridizes with the sequences complementary to sequences (i) or (ii), and optionally
(iv) sense mutations of neutral function in (i).

The invention also provides:
a polynucleotide, in particular DNA, which is capable of replication and comprises the nucleotide sequence as shown in SEQ ID No. 1;
a polynucleotide which codes for a polypeptide which comprises the amino acid sequence as shown in SEQ ID No. 2;
a vector containing parts of the polynucleotide according to the invention, at least 15 successive nucleotides of the sequence claimed
and coryneform bacteria in which the citB gene is attenuated, in particular by an insertion or deletion.

The invention also provides polynucleotides which substantially comprise a polynucleotide sequence, which are obtainable by screening by means of hybridization of a corresponding gene library of a coryneform bacterium, which comprises the complete gene or parts thereof, with a probe which comprises the sequence of the polynucleotide according to the invention or a fragment thereof, and isolation of the polynucleotide sequence mentioned.

BRIEF DESCRIPTION OF THE FIGURE

FIG. 1: Map of the plasmid pCR2.1citBint.

The abbreviations and designations used have the following meaning.
KmR: Kanamycin resistance gene
EcoRI: Cleavage site of the restriction enzyme EcoRI
HindIII: Cleavage site of the restriction enzyme HindIII
CitBint: Internal fragment of the citB gene
ColE1: Replication origin of the plasmid ColE1

DETAILED DESCRIPTION OF THE INVENTION

Polynucleotides comprising the sequences according to the invention are suitable as hybridization probes for RNA, cDNA and DNA, in order to isolate, in the full length, nucleic acids or polynucleotides or genes which code for the CitB protein or to isolate those nucleic acids or polynucleotides or genes which have a high similarity with the sequence of the citB gene. They are also suitable for incorporation into so-called "arrays", "micro arrays" or "DNA chips" in order to detect and determine the corresponding polynucleotides.

Polynucleotides comprising the sequences according to the invention are furthermore suitable as primers with the aid of which DNA of genes which code for the CitB protein can be prepared by the polymerase chain reaction (PCR).

Such oligonucleotides which serve as probes or primers comprise at least 30, preferably at least 20, very particularly preferably at least 15 successive nucleotides. Oligonucleotides which have a length of at least 40 or 50 nucleotides are also suitable.

"Isolated" means separated out of its natural environment.

"Polynucleotide" in general relates to polyribonucleotides and polydeoxyribonucleotides, it being possible for these to be non-modified RNA or DNA or modified RNA or DNA.

The polynucleotides according to the invention include a polynucleotide according to SEQ ID No. 1 or a fragment prepared therefrom and also those which are at least 70%, preferably at least 80% and in particular at least 90% to 95% identical to the polynucleotide according to SEQ ID No. 1 or a fragment prepared therefrom.

"Polypeptides" are understood as meaning peptides or proteins which comprise two or more amino acids bonded via peptide bonds.

The polypeptides according to the invention include a polypeptide according to SEQ ID No. 2, in particular those with the biological activity of the CitB protein, and also those which are at least 70%, preferably at least 80% and in particular at least 90% to 95% identical to the polypeptide according to SEQ ID No. 2 and have the activity mentioned.

The invention moreover provides a process for the fermentative preparation of amino acids, in particular L-lysine, using coryneform bacteria which in particular already produce amino acids, and in which the nucleotide sequences which code for the citB gene are attenuated, in particular eliminated or expressed at a low level.

The term "attenuation" in this connection describes the reduction or elimination of the intracellular activity of one or more enzymes (proteins) in a microorganism which are coded by the corresponding DNA, for example by using a weak promoter or using a gene or allele which codes for a corresponding enzyme with a low activity or inactivates the corresponding gene or enzyme (protein), and optionally combining these measures.

The microorganisms which the present invention provides can prepare amino acids, in particular L-lysine, from glucose, sucrose, lactose, fructose, maltose, molasses, starch, cellulose or from glycerol and ethanol. They can be representatives of coryneform bacteria, in particular of the genus *Corynebacterium*. Of the genus *Corynebacterium*, there may be mentioned in particular the species *Corynebacterium glutamicum*, which is known among experts for its ability to produce L-amino acids.

Suitable strains of the genus *Corynebacterium*, in particular of the species *Corynebacterium glutamicum* (*C. glutamicum*), are in particular the known wild-type strains

*Corynebacterium glutamicum* ATCC13032
*Corynebacterium acetoglutamicum* ATCC15806
*Corynebacterium acetoacidophilum* ATCC13870
*Corynebacterium melassecola* ATCC17965
*Corynebacterium thermoaminogenes* FERM BP-1539
*Brevibacterium flavum* ATCC14067
*Brevibacterium lactofermentum* ATCC13869 and
*Brevibacterium divaricatum* ATCC14020 or L-amino acid-producing mutants or strains prepared therefrom, such as, for example, the L-lysine-producing strains

*Corynebacterium glutamicum* FERM-P 1709
*Brevibacterium flavum* FERM-P 1708
*Brevibacterium lactofermentum* FERM-P 1712
*Corynebacterium glutamicum* FERM-P 6463
*Corynebacterium glutamicum* FERM-P 6464
*Corynebacterium glutamicum* DM58-1
*Corynebacterium glutamicum* DG52-5
*Corynebacterium glutamicum* DSM 5715 and
*Corynebacterium glutamicum* DSM 12866

The inventors have succeeded in isolating the new citB gene of *C. glutamicum* which codes for the CitB protein, which is a transcription regulator of a two-component system.

To isolate the citB gene or also other genes of *C. glutamicum*, a gene library of this microorganism is first set up in *Escherichia coli* (*E. coli*). The setting up of gene libraries is described in generally known textbooks and handbooks. The textbook by Winnacker: Gene und Klone, Eine Einführung in die Gentechnologie (Verlag Chemie, Weinheim, Germany, 1990) I.B.R., or the handbook by Sambrook et al.: Molecular Cloning, A Laboratory Manual (Cold Spring Harbor Laboratory Press, 1989) I.B.R. may be mentioned as an example. A well-known gene library is that of the *E. coli* K-12 strain W3110 set up in λ vectors by Kohara et al. (Cell 50, 495–508 (1987)) I.B.R. Bathe et al. (Molecular and General Genetics, 252:255–265, 1996) I.B.R. describe a gene library of *C. glutamicum* ATCC13032, which was set up with the aid of the cosmid vector SuperCos I (Wahl et al., 1987, Proceedings of the National Academy of Sciences USA, 84:2160–2164 I.B.R.) in the *E. coli* K-12 strain NM554 (Raleigh et al., 1988, Nucleic Acids Research 16:1563–1575 I.B.R.). Börmann et al. (Molecular Microbiology 6(3), 317–326)) (1992)) I.B.R. in turn describe a gene library of *C. glutamicum* ATCC13032 using the cosmid pHC79 (Hohn and Collins, 1980, Gene 11, 291–298) I.B.R.

To prepare a gene library of *C. glutamicum* in *E. coli* it is also possible to use plasmids such as pBR322 (Bolivar, 1979, Life Sciences, 25, 807–818 I.B.R.) or pUC9 (Vieira et al., 1982, Gene, 19:259–268 I.B.R.). Suitable hosts are, in particular, those *E. coli* strains which are restriction- and recombination-defective, such as, for example, the strain DH5α (Jeffrey H. Miller: "A Short Course in Bacterial Genetics, A Laboratory Manual and Handbook for *Escherichia coli* and Related Bacteria", Cold Spring Harbour Laboratory Press, 1992 I.B.R.).

The long DNA fragments cloned with the aid of cosmids or other λ-vectors can then be subcloned in turn into the usual vectors suitable for DNA sequencing.

Methods of DNA sequencing are described, inter alia, by Sanger et al. (Proceedings of the National Academy of Sciences of the United States of America USA, 74:5463–5467, 1977) I.B.R.

The resulting DNA sequences can then be investigated with known algorithms or sequence analysis programs, such as e.g. that of Staden (Nucleic Acids Research 14, 217–232 (1986)) I.B.R., that of Marck (Nucleic Acids Research 16, 1829–1836 (1988)) I.B.R. or the GCG program of Butler (Methods of Biochemical Analysis 39, 74–97 (1998)) I.B.R.

The new DNA sequence of *C. glutamicum* which codes for the citB gene and which, as SEQ ID No. 1, is a constituent of the present invention has been obtained in this manner. The amino acid sequence of the corresponding protein has furthermore been derived from the present DNA sequence by the methods described above. The resulting amino acid sequence of the citB gene product is shown in SEQ ID No. 2.

Coding DNA sequences which result from SEQ ID No. 1 by the degeneracy of the genetic code are also a constituent of the invention. In the same way, DNA sequences which hybridize with SEQ ID No. 1 or parts of SEQ ID No. 1 are a constituent of the invention. Conservative amino acid exchanges, such as e.g. exchange of glycine for alanine or of aspartic acid for glutamic acid in proteins, are furthermore known among experts as "sense mutations" which do not lead to a fundamental change in the activity of the protein, i.e. are of neutral function. It is furthermore known that changes on the N and/or C terminus of a protein cannot substantially impair or can even stabilize the function thereof. Information in this context can be found by the expert, inter alia, in Ben-Bassat et al. (Journal of Bacteriology 169:751–757 (1987)) I.B.R., in O'Regan et al. (Gene 77:237–251 (1989)) I.B.R., in Sahin-Toth et al. (Protein Sciences 3:240–247 (1994)) I.B.R., in Hochuli et al. (Bio/Technology 6:1321–1325 (1988)) I.B.R. and in known textbooks of genetics and molecular biology. Amino acid sequences which result in a corresponding manner from SEQ ID No. 2 are also a constituent of the invention.

Finally, DNA sequences which are prepared by the polymerase chain reaction (PCR) using primers which result from SEQ ID No. 1 are a constituent of the invention. Such oligonucleotides typically have a length of at least 15 nucleotides.

Instructions for identifying DNA sequences by means of hybridization can be found by the expert, inter alia, in the handbook "The DIG System Users Guide for Filter Hybridization" from Boehringer Mannheim GmbH (Mannheim, Germany, 1993) I.B.R. and in Liebl et al. (International Journal of Systematic Bacteriology 41: 255–260 (1991)) I.B.R. The hybridization takes place under stringent conditions, that is to say only hybrids in which the probe and target sequence, i. e. the polynucleotides treated with the probe, are at least 70% identical are formed. It is known that the stringency of the hybridization, including the washing steps, is influenced or determined by varying the buffer composition, the temperature and the salt concentration. The hybridization reaction is preferably carried out under a relatively low stringency compared with the washing steps (Hybaid Hybridisation Guide, Hybaid Limited, Teddington, UK, 1996) I.B.R. A 5×SSC buffer at a temperature of approx. 50–68° C., for example, can be employed for the hybridization reaction. Probes can also hybridize here with polynucleotides which are less than 70% identical to the sequence of the probe. Such hybrids are less stable and are removed by washing under stringent conditions. This can be achieved, for example, by lowering the salt concentration to 2×SSC and optionally subsequently 0.5×SSC (The DIG System User's Guide for Filter Hybridisation, Boehringer Mannheim, Mannheim, Germany, 1995 I.B.R.) a temperature of approx. 50–68° C. being established. Polynucleotide fragments which are, for example, at least 70% or at least 80% or at least 90% to 95% identical to the sequence of the probe employed can be isolated by increasing the hybridization temperature stepwise from 50 to 68° C. in steps of approx. 1–2° C. Further instructions on hybridization are obtainable on the market in the form of so-called kits (e.g. DIG Easy Hyb from Roche Diagnostics GmbH, Mannheim, Germany, Catalogue No. 1603558) I.B.R.

Instructions for amplification of DNA sequences with the aid of the polymerase chain reaction (PCR) can be found by the expert, inter alia, in the handbook by Gait: Oligonucleotide Synthesis: A Practical Approach (IRL Press, Oxford, UK, 1984) I.B.R. and in Newton and Graham: PCR (Spektrum Akademischer Verlag, Heidelberg, Germany, 1994) I.B.R.

In the work on the present invention, it has been found that coryneform bacteria produce amino acids, in particular L-lysine, in an improved manner after attenuation of the citB gene.

To achieve an attenuation, either the expression of the citB gene or the catalytic properties of the enzyme protein can be reduced or eliminated. The two measures can optionally be combined.

The reduction in gene expression can take place by suitable culturing or by genetic modification (mutation) of the signal structures of gene expression. Signal structures of gene expression are, for example, repressor genes, activator genes, operators, promoters, attenuators, ribosome binding sites, the start codon and terminators. The expert can find information on this e.g. in the patent application WO 96/15246 I.B.R., in Boyd and Murphy (Journal of Bacteriology 170: 5949 (1988)) I.B.R., in Voskuil and Chambliss (Nucleic Acids Research 26: 3548 (1998) I.B.R., in Jensen and Hammer (Biotechnology and Bioengineering 58: 191 (1998)) I.B.R., in Pátek et al. (Microbiology 142: 1297 (1996)) I.B.R., Vasicova et al. (Journal of Bacteriology 181: 6188 (1999)) I.B.R. and in known textbooks of genetics and molecular biology, such as e.g. the textbook by Knippers ("Molekulare Genetik ", 6th edition, Georg Thieme Verlag, Stuttgart, Germany, 1995) I.B.R. or that by Winnacker ("Gene und Klone", VCH Verlagsgesellschaft, Weinheim, Germany, 1990) I.B.R.

Mutations which lead to a change or reduction in the catalytic properties of enzyme proteins are known from the prior art; examples which may be mentioned are the works by Qiu and Goodman (Journal of Biological Chemistry 272: 8611–8617 (1997)) I.B.R., Sugimoto et al. (Bioscience Biotechnology and Biochemistry 61: 1760–1762 (1997)) I.B.R. and Möckel ("Die Threonindehydratase aus *Corynebacterium glutamicum*: Aufhebung der allosterischen Regulation und Struktur des Enzyms", Reports from the Jülich Research Centre, Jül-2906, ISSN09442952, Jülich, Germany, 1994) I.B.R. Summarizing descriptions can be found in known textbooks of genetics and molecular biology, such as e.g. that by Hagemann ("Allgemeine Genetik", Gustav Fischer Verlag, Stuttgart, 1986) I.B.R.

Possible mutations are transitions, transversions, insertions and deletions. Depending on the effect of the amino acid exchange on the enzyme activity, missense mutations or nonsense mutations are referred to. Insertions or deletions of at least one base pair (bp) in a gene lead to frame shift mutations, as a consequence of which incorrect amino acids are incorporated or translation is interrupted prematurely. Deletions of several codons typically lead to a complete loss of the enzyme activity. Instructions on generation of such mutations are prior art and can be found in known textbooks of genetics and molecular biology, such as e.g. the textbook by Knippers ("Molekulare Genetik", 6th edition, Georg Thieme Verlag, Stuttgart, Germany, 1995) I.B.R., that by Winnacker ("Gene und Klone", VCH Verlagsgesellschaft, Weinheim, Germany, 1990) I.B.R. or that by Hagemann ("Allgemeine Genetik", Gustav Fischer Verlag, Stuttgart, 1986) I.B.R.

A common method of mutating genes of *C. glutamicum* is the method of gene disruption and gene replacement described by Schwarzer and Pühler (Bio/Technology 9, 84–87 (1991)) I.B.R.

In the method of gene disruption a central part of the coding region of the gene of interest is cloned in a plasmid vector which can replicate in a host (typically *E. coli*), but not in *C. glutamicum*. Possible vectors are, for example, pSUP301 (Simon et al., Bio/Technology 1, 784–791 (1983) I.B.R.), pK18mob or pK19mob (Schäfer et al., Gene 145, 69–73 (1994) I.B.R.), pK18mobsacB or pK19mobsacB (Jäger et al., Journal of Bacteriology 174: 5462–65 (1992) I.B.R.), pGEM-T (Promega corporation, Madison, Wis., USA), pCR2.1-TOPO (Shuman (1994) I.B.R.). Journal of Biological Chemistry 269:32678–84 I.B.R.; U.S. Pat. No. 5,487,993 I.B.R.), pCR®Blunt (Invitrogen, Groningen, Holland; Bernard et al., Journal of Molecular Biology, 234: 534–541 (1993) I.B.R.) or pEM1 (Schrumpf et al, 1991, Journal of Bacteriology 173:4510–4516 I.B.R.). The plasmid vector which contains the central part of the coding region of the gene is then transferred into the desired strain of *C. glutamicum* by conjugation or transformation. The method of conjugation is described, for example, by Schäfer et al. (Applied and Environmental Microbiology 60, 756–759 (1994) I.B.R.). Methods for transformation are described, for example, by Thierbach et al. (Applied Microbiology and Biotechnology 29, 356–362 (1988) I.B.R.), Dunican and Shivnan (Bio/Technology 7, 1067–1070 (1989)) I.B.R. and Tauch et al. (FEMS Microbiological Letters 123, 343–347 (1994)) I.B.R. After homologous recombination by means of a "cross-over" event, the coding region of the gene in question is interrupted by the vector sequence and two incomplete alleles are obtained, one lacking the 3' end and one lacking the 5' end. This method has been used, for example, by Fitzpatrick et al. (Applied Microbiology and Biotechnology 42, 575–580 (1994) I.B.R.) to eliminate the recA gene of C. glutamicum.

In the method of gene replacement, a mutation, such as e.g. a deletion, insertion or base exchange, is established in vitro in the gene of interest. The allele prepared is in turn cloned in a vector which is not replicative for C. glutamicum and this is then transferred into the desired host of C. glutamicum by transformation or conjugation. After homologous recombination by means of a first "cross-over" event which effects integration and a suitable second "cross-over" event which effects excision in the target gene or in the target sequence, the incorporation of the mutation or of the allele is achieved. This method was used, for example, by Peters-Wendisch et al. (Microbiology 144, 915–927 (1998)) I.B.R. to eliminate the pyc gene of C. glutamicum by a deletion.

A deletion, insertion or a base exchange can be incorporated into the citB gene in this manner.

In addition, it may be advantageous for the production of L-amino acids, in particular L-lysine, to enhance, in particular to over-express, one or more enzymes of the particular biosynthesis pathway, of glycolysis, of anaplerosis, of the citric acid cycle, of the pentose phosphate cycle, of amino acid export and optionally regulatory proteins, in addition to attenuation of the citB gene.

The term "enhancement" in this connection describes the increase in the intracellular activity of one or more enzymes (proteins) in a microorganism which are coded by the corresponding DNA, for example by increasing the number of copies of the gene or genes, using a potent promoter or using a gene or allele which codes for a corresponding enzyme (protein) having a high activity, and optionally combining these measures.

Thus, for example, for the preparation of L-lysine, at the same time one or more of the genes chosen from the group consisting of the dapA gene which codes for dihydrodipicolinate synthase (EP-B 0 197 335 I.B.R.), the gap gene which codes for glyceraldehyde 3-phosphate dehydrogenase (Eikmanns (1992), Journal of Bacteriology 174:6076–6086 I.B.R.), the zwf gene which codes for glucose 6-phosphate dehydrogenase (JP-A-09224661 I.B.R.), the pyc gene which codes for pyruvate carboxylase (DE-A-198 31 609 I.B.R.), the lysE gene which codes for lysine export (DE-A-195 48 222 I.B.R.)

the lysc gene which codes for a feed back resistant aspartate kinase (EP-B-0387527 I.B.R.; EP-A-0699759 I.B.R.; WO 00/63388 I.B.R.), or the zwa1 gene which codes for the Zwa1 protein (DE: 199 59 328.0 I.B.R., DSM 13115)

can be enhanced, in particular over-expressed.

It may furthermore be advantageous for the production of amino acids, in particular L-lysine, in addition to the attenuation of the citB gene, for one or more of the genes chosen from the group consisting of the pck gene which codes for phosphoenol pyruvate carboxykinase (DE 199 50 409.1 I.B.R., DSM 13047), the pgi gene which codes for glucose 6-phosphate isomerase (U.S. Ser. No. 09/396,478 I.B.R., DSM 12969), the poxB gene which codes for pyruvate oxidase (DE:1995 1975.7 I.B.R., DSM 13114)

the zwa2 gene which codes for the Zwa2 protein (DE: 19959327.2 I.B.R., DSM 13113)

to be attenuated at the same time.

In addition to attenuation of the citB gene it may furthermore be advantageous, for the production of amino acids, in particular L-lysine, to eliminate undesirable side reactions, (Nakayama: "Breeding of Amino Acid Producing Microorganisms", in: Overproduction of Microbial Products, Krumphanzl, Sikyta, Vanek (eds.), Academic Press, London, UK, 1982 I.B.R.).

The invention also provides the microorganisms prepared according to the invention, and these can be cultured continuously or discontinuously in the batch process (batch culture) or in the fed batch (feed process) or repeated fed batch process (repetitive feed process) for the purpose of production of L-amino acids, in particular L-lysine. A summary of known culture methods is described in the textbook by Chmiel (Bioprozesstechnik 1. Einführung in die Bioverfahrenstechnik (Gustav Fischer Verlag, Stuttgart, 1991) I.B.R.) or in the textbook by Storhas (Bioreaktoren und periphere Einrichtungen (Vieweg Verlag, Braunschweig/Wiesbaden, 1994) I.B.R.).

The culture medium to be used must meet the requirements of the particular strains in a suitable manner. Descriptions of culture media for various microorganisms are contained in the handbook "Manual of Methods for General Bacteriology" of the American Society for Bacteriology (Washington D.C., USA, 1981) I.B.R. Sugars and carbohydrates, such as e.g. glucose, sucrose, lactose, fructose, maltose, molasses, starch and cellulose, oils and fats, such as, for example, soya oil, sunflower oil, groundnut oil and coconut fat, fatty acids, such as, for example, palmitic acid, stearic acid and linoleic acid, alcohols, such as, for example, glycerol and ethanol, and organic acids, such as, for example, acetic acid, can be used as the source of carbon. These substances can be used individually or as a mixture.

Organic nitrogen-containing compounds, such as peptones, yeast extract, meat extract, malt extract, corn steep liquor, soya bean flour and urea, or inorganic compounds, such as ammonium sulfate, ammonium chloride, ammonium phosphate, ammonium carbonate and ammonium nitrate, can be used as the source of nitrogen. The sources of nitrogen can be used individually or as a mixture.

Phosphoric acid, potassium dihydrogen phosphate or dipotassium hydrogen phosphate or the corresponding sodium-containing salts can be used as the source of phosphorus. The culture medium must furthermore comprise salts of metals, such as, for example, magnesium sulfate or iron sulfate, which are necessary for growth. Finally, essential growth substances, such as amino acids and vitamins, can be employed in addition to the abovementioned substances. Suitable precursors can moreover be added to the culture medium. The starting substances mentioned can be added to the culture in the form of a single batch, or can be fed in during the culture in a suitable manner.

Basic compounds, such as sodium hydroxide, potassium hydroxide, ammonia or aqueous ammonia, or acid compounds, such as phosphoric acid or sulfuric acid, can be employed in a suitable manner to control the pH of the culture. Antifoams, such as, for example, fatty acid polyglycol esters, can be employed to control the development of foam. Suitable substances having a selective action, such as, for example, antibiotics, can be added to the medium to maintain the stability of plasmids. To maintain aerobic conditions, oxygen or oxygen-containing gas mixtures, such as, for example, air, are introduced into the culture. The temperature of the culture is usually 20° C. to 45° C., and preferably 25° C. to 40° C. Culturing is continued until a maximum of the desired product has formed. This target is usually reached within 10 hours to 160 hours.

Methods for the determination of L-amino acids are known from the prior art. The analysis can thus be carried out, for example, as described by Spackman et al. (Analytical Chemistry, 30, (1958), 1190) I.B.R. by anion exchange chromatography with subsequent ninhydrin derivatization, or it can be carried out by reversed phase HPLC, for example as described by Lindroth et al. (Analytical Chemistry (1979) 51: 1167–1174) I.B.R.

The invention furthermore relates to a process for the fermentative preparation of an amino acid chosen from the group consisting of L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan and L-arginine, in particular L-lysine, using coryneform bacteria which in particular already produce one or more of the amino acids mentioned.

The following microorganism was deposited on 23.08.2000 as a pure culture at the Deutsche Sammlung für Mikroorganismen und Zellkulturen (DSMZ=German Collection of Microorganisms and Cell Cultures, Braunschweig, Germany) in accordance with the Budapest Treaty:
Escherichia coli strain Top10/pCR2.1citBint as DSM 13672.

The present invention is explained in more detail in the following with the aid of embodiment examples.

The isolation of plasmid DNA from *Escherichia coli* and all techniques of restriction, Klenow and alkaline phosphatase treatment were carried out by the method of Sambrook et al. (Molecular Cloning. A Laboratory Manual, 1989, Cold Spring Harbour Laboratory Press, Cold Spring Harbor, N.Y., USA) I.B.R. Methods for transformation of *Escherichia coli* are also described in this handbook.

The composition of the usual nutrient media, such as LB or TY medium, can also be found in the handbook by Sambrook et al.

EXAMPLE 1
Preparation of a Genomic Cosmid Gene Library from *C. glutamicum* ATCC 13032

Chromosomal DNA from *C. glutamicum* ATCC 13032 was isolated as described by Tauch et al. (1995, Plasmid 33:168–179) I.B.R. and partly cleaved with the restriction enzyme Sau3AI (Amersham Pharmacia, Freiburg, Germany, Product Description Sau3AI, Code no. 27-0913-02). The DNA fragments were dephosphorylated with shrimp alkaline phosphatase (Roche Molecular Biochemicals, Mannheim, Germany, Product Description SAP, Code no. 1758250). The DNA of the cosmid vector SuperCos1 (Wahl et al. (1987), Proceedings of the National Academy of Sciences, USA 84:2160–2164 I.B.R.), obtained from Stratagene (La Jolla, USA, Product Description SuperCos1 Cosmid Vector Kit, Code no. 251301) was cleaved with the restriction enzyme XbaI (Amersham Pharmacia, Freiburg, Germany, Product Description XbaI, Code no. 27-0948-02) and likewise dephosphorylated with shrimp alkaline phosphatase.

The cosmid DNA was then cleaved with the restriction enzyme BamHI (Amersham Pharmacia, Freiburg, Germany, Product Description BamHI, Code no. 27-0868-04). The cosmid DNA treated in this manner was mixed with the treated ATCC13032 DNA and the batch was treated with T4 DNA ligase (Amersham Pharmacia, Freiburg, Germany, Product Description T4-DNA-Ligase, Code no. 27-0870-04). The ligation mixture was then packed in phages with the aid of Gigapack II XL Packing Extract (Stratagene, La Jolla, USA, Product Description Gigapack II XL Packing Extract, Code no. 200217).

For infection of the *E. coli* strain NM554 (Raleigh et al. 1988, Nucleic Acid Res. 16:1563–1575 I.B.R.) the cells were taken up in 10 mM MgSO$_4$ and mixed with an aliquot of the phage suspension. The infection and titering of the cosmid library were carried out as described by Sambrook et al. (1989, Molecular Cloning: A Laboratory Manual, Cold Spring Harbor I.B.R.), the cells being plated out on LB agar (Lennox, 1955, Virology, 1:190 I.B.R.)+100 μg/ml ampicillin. After incubation overnight at 37° C., recombinant individual clones were selected.

EXAMPLE 2
Isolation and Sequencing of the citB Gene

The cosmid DNA of an individual colony was isolated with the Qiaprep Spin Miniprep Kit (Product No. 27106, Qiagen, Hilden, Germany) in accordance with the manufacturer's instructions and partly cleaved with the restriction enzyme Sau3AI (Amersham Pharmacia, Freiburg, Germany, Product Description Sau3AI, Product No. 27-0913-02). The DNA fragments were dephosphorylated with shrimp alkaline phosphatase (Roche Molecular Biochemicals, Mannheim, Germany, Product Description SAP, Product No. 1758250). After separation by gel electrophoresis, the cosmid fragments in the size range of 1500 to 2000 bp were isolated with the QiaExII Gel Extraction Kit (Product No. 20021, Qiagen, Hilden, Germany).

The DNA of the sequencing vector pZero-1, obtained from Invitrogen (Groningen, The Netherlands, Product Description Zero Background Cloning Kit, Product No. K2500-01) was cleaved with the restriction enzyme BamHI (Amersham Pharmacia, Freiburg, Germany, Product Description BamHI, Product No. 27-0868-04). The ligation of the cosmid fragments in the sequencing vector pZero-1 was carried out as described by Sambrook et al. (1989, Molecular Cloning: A Laboratory Manual, Cold Spring Harbor I.B.R.), the DNA mixture being incubated overnight with T4 ligase (Pharmacia Biotech, Freiburg, Germany). This ligation mixture was then electroporated (Tauch et al. 1994, FEMS Microbiol Letters, 123:343–7 I.B.R.) into the *E. coli* strain DH5αMCR (Grant, 1990, Proceedings of the National Academy of Sciences, U.S.A., 87:4645–4649 I.B.R.) and plated out on LB agar (Lennox, 1955, Virology, 1:190 I.B.R.) with 50 μg/ml zeocin.

The plasmid preparation of the recombinant clones was carried out with the Biorobot 9600 (Product No. 900200, Qiagen, Hilden, Germany). The sequencing was carried out by the dideoxy chain termination method of Sanger et al. (1977, Proceedings of the National Academies of Sciences, U.S.A., 74:5463–5467 I.B.R.) with modifications according to Zimmermann et al. (1990, Nucleic Acids Research, 18:1067) I.B.R. The "RR dRhodamin Terminator Cycle Sequencing Kit" from PE Applied Biosystems (Product No. 403044, Weiterstadt, Germany) was used. The separation by gel electrophoresis and analysis of the sequencing reaction were carried out in a "Rotiphoresis NF Acrylamide/Bisacrylamide" Gel (29:1) (Product No. A124.1, Roth, Karlsruhe, Germany) with the "ABI Prism 377" sequencer from PE Applied Biosystems (Weiterstadt, Germany).

The raw sequence data obtained were then processed using the Staden program package (1986, Nucleic Acids Research, 14:217–231 I.B.R.) version 97-0. The individual sequences of the pZero1 derivatives were assembled to a continuous contig. The computer-assisted coding region analyses were prepared with the XNIP program (Staden, 1986, Nucleic Acids Research, 14:217–231 I.B.R.). Further analyses were carried out with the "BLAST search program" (Altschul et al., 1997, Nucleic Acids Research, 25:3389–3402 I.B.R.) against the non-redundant databank of the "National Center for Biotechnology Information" (NCBI, Bethesda, Md., USA).

The resulting nucleotide sequence is shown in SEQ ID No. 1. Analysis of the nucleotide sequence showed an open reading frame of 657 base pairs, which was called the citB gene. The citB gene codes for a polypeptide of 219 amino acids.

EXAMPLE 3
Preparation of an Integration Vector for Integration Mutagenesis of the citB Gene From the strain ATCC 13032, chromosomal DNA was isolated by the method of Eikmanns et al. (Microbiology 140: 1817–1828 (1994)) I.B.R. On the basis of the sequence of the citB gene known for *C. glutamicum* from example 2, the following oligonucleotides were chosen for the polymerase chain reaction (see SEQ ID No. 4 and SEQ ID No. 5):

citB-int1: 5' CCC GGA TCT CCT ACT TGT TG 3' (SEQ ID NO: 4)
citB-int2: 5' TCT GTG GCG GAT CTA GAG AC 3' (SEQ ID NO: 5)

The primers shown were synthesized by MWG Biotech (Ebersberg, Germany) and the PCR reaction was carried out by the standard PCR method of Innis et al. (PCR protocols. A guide to methods and applications, 1990, Academic Press I.B.R.) with the Taq-polymerase from Boehringer Mannheim (Germany, Product Description Taq DNA polymerase, Product No. 1 146 165). With the aid of the polymerase chain reaction, the primers allow amplification of an internal fragment of the citB gene 318 bp in size. The product amplified in this way was tested electrophoretically in a 0.8% agarose gel.

The amplified DNA fragment (see SEQ ID No. 3) was ligated with the TOPO TA Cloning Kit from Invitrogen Corporation (Carlsbad, Calif., USA; Catalogue Number K4500-01) in the vector pCR2.1-TOPO (Mead at al. (1991) Bio/Technology 9:657–663 I.B.R.).

The *E. coli* strain TOP10 was then electroporated with the ligation batch (Hanahan, Ind.: DNA cloning. A practical approach. Vol. I. IRL-Press, Oxford, Washington D.C., USA, 1985 I.B.R.). Selection of plasmid-carrying cells was carried out by plating out the transformation batch on LB Agar (Sambrook et al., Molecular cloning: a laboratory manual. $2^{nd}$ Ed. Cold Spring Harbor Laboratory Press, Cold Spring Harbor, N.Y., 1989 I.B.R.), which had been supplemented with 50 mg/l kanamycin. Plasmid DNA was isolated from a transformant with the aid of the QIAprep Spin Miniprep Kit from Qiagen and checked by restriction with the restriction enzyme EcoRI and subsequent agarose gel electrophoresis (0.8%). The plasmid was called pCR2.1citBint and is shown in FIG. 1.

EXAMPLE 4
Integration Mutagenesis of the citB Gene in the Strains DSM 5715 and FERM-BP 1763

The vector pCR2.1citBint mentioned in example 3 was electroporated by the electroporation method of Tauch et al. (FEMS Microbiological Letters, 123:343–347 (1994) I.B.R.) into the strains *Corynebacterium glutamicum* DSM 5715 and *Brevibacterium lactofermentum* FERM-BP 1763. The strain DSM 5715 is an AEC-resistant lysine producer (EP-B-0435132 I.B.R.), and the strain FERM-BP 1763 is a mycophenolic acid-resistant valine producer (U.S. Pat. No. 5,188,948 I.B.R.). The vector pCR2.1citBint cannot replicate independently in DSM5715 and FERM-BP 1763 and is retained in the cell only if it has integrated into the chromosome of DSM 5715 or FERM-BP 1763. Selection of clones with pCR2.1citBint integrated into the chromosome was carried out by plating out the electroporation batch on LB agar (Sambrook et al., Molecular cloning: a laboratory manual. $2^{nd}$ Ed. Cold Spring Harbor Laboratory Press, Cold Spring Harbor, N.Y. I.B.R. I.B.R.), which had been supplemented with 15 mg/l kanamycin.

For detection of the integration, the citBint fragment was labelled with the Dig hybridization kit from Boehringer by the method of "The DIG System Users Guide for Filter Hybridization" of Boehringer Mannheim GmbH (Mannheim, Germany, 1993 I.B.R.). Chromosomal DNA of in each case a potential integrant was isolated by the method of Eikmanns et al. (Microbiology 140: 1817–1828 (1994) I.B.R.) and in each case cleaved with the restriction enzymes EcoRI, BamHI and HindIII. The fragments formed were separated by means of agarose gel electrophoresis and hybridized at 68° C. with the Dig hybridization kit from Boehringer. The plasmid pCR2.1citBint mentioned in example 3 had been inserted into the chromosome of DSM5715 and into the chromosome of FERM-BP 1763 within the chromosomal citB gene. The strains were called DSM5715::pCR2.1citBint and FERM-BP 1763::pCR2.1citBint.

EXAMPLE 5
Preparation of Lysine

The *C. glutamicum* strain DSM5715::pCR2.1citBint obtained in example 4 was cultured in a nutrient medium suitable for the production of lysine and the lysine content in the culture supernatant was determined.

For this, the strain was first incubated on an agar plate with the corresponding antibiotic (brain-heart agar with kanamycin (25 mg/l) for 24 hours at 33° C. Starting from this agar plate culture, a preculture was seeded (10 ml medium in a 100 ml conical flask). The complete medium CgIII was used as the medium for the preculture.

| Medium Cg III | |
| --- | --- |
| NaCl | 2.5 g/l |
| Bacto-Peptone | 10 g/l |
| Bacto-Yeast extract | 10 g/l |
| Glucose (autoclaved separately) | 2% (w/v) |

The pH is brought to pH 7.4

Kanamycin (25 mg/l) was added to this. The preculture was incubated for 16 hours at 33° C. at 240 rpm on a shaking machine. A main culture was seeded from this preculture such that the initial OD (660 nm) of the main culture is 0.1 OD. The medium MM-L was used for the main culture.

| Medium MM-L | |
|---|---|
| CSL (corn steep liquor) | 5 g/l |
| MOPS (morpholinopropanesulfonic acid) | 20 g/l |
| Glucose (autoclaved separately) | 50 g/l |
| Salts: | |
| $(NH_4)_2SO_4$ | 25 g/l |
| $KH_2PO_4$ | 0.1 g/l |
| $MgSO_4 * 7\ H_2O$ | 1.0 g/l |
| $CaCl_2 * 2\ H_2O$ | 10 mg/l |
| $FeSO_4 * 7\ H_2O$ | 10 mg/l |
| $MnSO_4 * H_2O$ | 5.0 mg/l |
| Biotin (sterile-filtered) | 0.3 mg/l |
| Thiamine*HCl (sterile-filtered) | 0.2 mg/l |
| Leucine (sterile-filtered) | 0.1 g/l |
| $CaCO_3$ | 25 g/l |

The CSL, MOPS and the salt solution were brought to pH 7 with aqueous ammonia and autoclaved. The sterile substrate, amino acid and vitamin solutions, as well as the $CaCO_3$ autoclaved in the dry state were then added.

Culturing was carried out in a 10 ml volume in a 100 ml conical flask with baffles. Kanamycin (25 mg/l) was added. Culturing was carried out at 33° C. and 80% atmospheric humidity.

After 72 hours, the OD was determined at a measurement wavelength of 660 nm with a Biomek 1000 (Beckmann Instruments GmbH, Munich). The amount of lysine formed was determined with an amino acid analyzer from Eppendorf-BioTronik (Hamburg, Germany) by ion exchange chromatography and post-column derivatization with ninhydrin detection.

The result of the experiment is shown in table 1.

TABLE 1

| Strain | CD (660 nm) | Lysine HCl g/l |
|---|---|---|
| DSM5715 | 7.5 | 13.3 |
| DSM5715::pCR2.1citBint | 7.6 | 14.4 |

Example 6

Preparation of Valine

The *B. lactofermentum* strain FERM-BP 1763::pCR2.1citBint obtained in example 4 was cultured in a nutrient medium suitable for the production of valine and the valine content in the culture supernatant was determined.

For this, the strain was first incubated on an agar plate with the corresponding antibiotic (brain-heart agar with kanamycin (25 mg/l) for 24 hours at 33° C. Starting from this agar plate culture, a preculture was seeded (10 ml medium in a 100 ml conical flask). The complete medium CgIII was used as the medium for the preculture. Kanamycin (25 mg/l) was added to this. The preculture was incubated for 16 hours at 33° C. at 240 rpm on a shaking machine. A main culture was seeded from this preculture such that the initial OD (660 nm) of the main culture was 0.1 OD. The medium MM-V was used for the main culture.

| Medium MM-V | |
|---|---|
| CSL (corn steep liquor) | 5 g/l |
| MOPS (morpholinopropanesulfonic acid) | 20 g/l |
| Glucose (autoclaved separately) | 50 g/l |
| Salts: | |
| $(NH_4)_2SO_4)$ | 25 g/l |
| $KH_2PO_4$ | 0.1 g/l |
| $MgSO_4 * 7\ H_2O$ | 1.0 g/l |
| $CaCl_2 * 2\ H_2O$ | 10 mg/l |
| $FeSO_4 * 7\ H_2O$ | 10 mg/l |
| $MnSO_4 * H_2O$ | 5.0 mg/l |
| Isoeucine (sterile-filtered) | 0.1 g/l |
| Methionine (sterile-filtered) | 0.1 g/l |
| Thiamine*HCl (sterile-filtered) | 0.2 mg/l |
| Leucine (sterile-filtered) | 0.1 g/l |
| $CaCO_3$ | 25 g/l |

The CSL (corn steep liquor), MOPS (morpholinopropanesulfonic acid) and the salt solution were brought to pH 7 with aqueous ammonia and autoclaved. The sterile substrate, amino acid and vitamin solutions, as well as the $CaCO_3$ autoclaved in the dry state were then added.

Culturing was carried out in a 10 ml volume in a 100 ml conical flask with baffles. Kanamycin (25 mg/l) was added. Culturing was carried out at 33° C. and 80% atmospheric humidity.

After 48 hours, the OD was determined at a measurement wavelength of 660 nm with a Biomek 1000 (Beckmann Instruments GmbH, Munich). The amount of valine formed was determined with an amino acid analyzer from Eppendorf-BioTronik (Hamburg, Germany) by ion exchange chromatography and post-column derivatization with ninhydrin detection.

The result of the experiment is shown in table 2.

TABLE 2

| Strain | OD (660 nm) | Valine HCl g/l |
|---|---|---|
| FERM-BP 1763 | 12.1 | 7.5 |
| FERM-BP 1763::pCR2.1citBint | 13.3 | 11.3 |

This application claims priority to German Priority Document Application No. 100 42 741.3, filed on Aug. 31, 2000 and to German Priority Document Application No. 101 08 841.8, filed on Feb. 23, 2001. Both German Priority Documents are hereby incorporated by reference in their entirety.

We claim:

1. An isolated polynucleotide wherein the polynucleotide encodes a polypeptide which comprises the amino acid sequence shown in SEQ ID No. 2.

2. A vector comprising the polynucleotide of SEQ ID. No: 3.

3. An isolated polynucleotide comprising the nucleic acid as shown in SEQ ID No: 3.

4. A Coryneform bacterium comprising a vector which includes the polynucleotide according to claim 1.

5. A polynucleotide fragment of the polynucleotide of SEQ ID NO: 1 comprising at least 30 consecutive nucleotides of SEQ ID NO: 1.

6. A bacterium comprising the isolated polynucleotide according to claim 1.

7. The bacterium according to claim 6, wherein the bacterium is a *corynebacterium* or an *Escherichia coli*.

8. A bacterium comprising the vector of claim 2 and deposited under DSM 13672.

9. The polynucleotide according to claim 1, wherein the polynucleotide is a DNA.

10. The polynucleotide according to claim 1, wherein the polynucleotide is an RNA.

11. An isolated polynucleotide comprising the nucleic acid sequence as shown in SEQ ID No. 1.

* * * * *